United States Patent [19]

Dumenek et al.

[11] Patent Number: 5,024,652
[45] Date of Patent: Jun. 18, 1991

[54] OPHTHALMOLOGICAL DEVICE

[76] Inventors: Vladimir A. Dumenek, prospekt Gagarina, 216, kv. 38, Gorky; Georgy E. Stolyarenko, ulitsa Ramenki, 9, korpus 1, kv. 1, Moscow; Leopold V. Kossovsky, ulitsa Usilova, 1, korpus 3, kv. 15, Gorky, all of U.S.S.R.

[21] Appl. No.: 525,304

[22] Filed: May 17, 1990

Related U.S. Application Data

[63] Continuation of Ser. No. 248,968, Sep. 26, 1988, abandoned.

[51] Int. Cl.5 .............................................. A61B 17/20
[52] U.S. Cl. ..................................... 604/22; 606/170; 606/174
[58] Field of Search ................... 604/22; 606/170, 171, 606/174, 175

[56] References Cited

U.S. PATENT DOCUMENTS 3,763,864 10/1973 Dremann ............................ 604/171
3,776,238 12/1973 Peyman et al. .
3,884,238 5/1975 O'Malley et al. .
4,672,965 6/1987 Baum .................................... 604/22
4,764,165 8/1988 Reimels et al. ....................... 604/22

FOREIGN PATENT DOCUMENTS 980710 5/1980 U.S.S.R. .

Primary Examiner—Max Hindenburg
Assistant Examiner—Michael Rafa
Attorney, Agent, or Firm—Ladas & Parry

[57] ABSTRACT

The device comprises a surgical instrument incorporating a movable element and a stationary element, and a drive made as a closed hydraulic system adapted to effect mutual displacement of the elements.

13 Claims, 2 Drawing Sheets

OPHTHALMOLOGICAL DEVICE

This is a continuation of copending application Ser. No. 07/248,968 filed on Sept. 26, 1988, now abandoned.

FIELD OF THE INVENTION

The invention relates generally to medical equipment and more specifically to ophthalmological devices.

The invention is applicable for removal of vitreous humor, soft cataracts, preretinal membranes, and other pathologically affected intraocular structures, as well as foreign bodies.

BACKGROUND OF THE INVENTION

Over the past few years widespread use has been gained in opthalmosurgery by surgical instruments for carrying out intraocular surgery through a small (under 1.5 mm) incision in the ocular wall.

One state-of-the-art ophthalmological instrument is known, which is in fact a cutting instrument executing reciprocation motion and having a channel for the vitreous humor to aspirate. The cutting knife of the instrument shaped as a hollow tube receives reciprocating motion from an electric motor accommodated in the instrument grip. The knife is coaxially mounted in the outer tube having one closed end to form a working endpiece together therewith, an opening being provided in the side wall of the outer tube close to its end (U.S. Pat. No. 4,108,182).

The intraocular tissue to be removed is sucked into the interior space of the outer tube by virtue of a negative pressure built up in the hollow inner tube and imparted through its open end to the opening in the outer tube. When extended the knife pointed end, while closing the opening in the outer tube, cuts off the tissue located inside the tube, whereupon the cut-off tissue is removed from the eye by aspiration. Then the knife returns into the initial position, thus exposing the opening in the outer tube, and the whole operating cycle is repeated.

However, the fact that the drive is accommodated in the instrument handgrip adds to its weight and causes parasitic vibrations of the working endpiece. Besides, provision of an electric motor in the instrument makes its sterilization difficult. The instrument construction makes no provision for adjusting the working stroke and the force applied to biological tissues.

One prior-art ophthalmological instrument features its working endpiece made up of two tubes in a manner described above, while a drive which is in fact an electromagnet, is brought outside the handgrip and is associated with the endpiece through a flexible tie-rod enclosed in a sheath (SU, A, 980,710). However, the aforesaid instrument is very sensitive to flexures of the flexible tie-rod which are inevitable in the course of surgery. Such sensitivity is causative of higly undesirable variations of the working endpiece stroke amplitude. In addition, bad vibrations are imparted to the working endpiece due to elctromagnet kicks.

One more ophthalmological device known in the present state of the art is adopted as the prototype; it comprises a cutting instrument in the form of a working endpiece which incorporates a stationary fixed outer tube having a closed free end and a side hole nearby said end, and an inner tube, which is in fact a movable element of the cutting instrument, having a pointed free end and being capable of reciprocating motion. The working endpiece may be made as microscissors. The device comprises also a handgrip on which is fixed the working endpiece and which accommodates a part of the drive made as a bellows mechanically associated with the movable element and connected to the flexible tube.

The drive is in fact a pneumatic system consisting of a compressor, control members of said compressor, and a flexible tube whose one end communicates with the compressor and the other end, with the bellows accommodated in the handgrip (U.S. Pat. No. 3,884,238).

Since the endpiece is introduced directly into the operative field the output power of the pneumatic drive is limited, whereby the drive fails to provide an adequate force applied to the movable element which is required, in particular, for cutting through dense intraocular tissues, e.g., the pupillary membranes, fibrous vitreous adhesions, and some other similar tissues. Besides, such a drive is unadaptable to adequately reliable forceps for gripping foreign bodies or membranous cataracts. Attempts aimed at increasing the drive power by elevating air pressure in the pneumatic drive are fraught with a danger of air inrush into the operative field. Moreover, the operating chain 'control pedal - electric control circuit - compressor - valving system - power fluid (air being known as highly compressible working fluid) - bellows - working end-piece movable element' features but inadequately quick action. This in turn results in that surgeon's decisions are executed with some delay in the course of surgery.

The surgeon is rather inflexibly bound to the mode of the device operation, since the operating modes are changed on the control panel, which involves the presence of a technically skilful operator in the operating room.

The scope of the disadvantages mentioned above results in that the surgeon has but an inadequate direct control over the operation of the device, i.e., he has to rely upon such factors as reliability and operating capabilities of a complicated electromechanical arrangement, promptness and adequate comprehension of auxiliary attending personnel stable operation of power mains, and some other, which are far from ensuring exact and instantaneous execution of surgeon's decisions. In its turn an inadequate direct surgeon's control over the operation of the instrument leads to affected safety of intraocular surgery and lower efficacy thereof in cases where surgeon's decisions fail to be executed in a full scope due to its going beyond the limits of the instrument capabilities.

SUMMARY OF THE INVENTION

It is an object of the invention to provide an ophthalmological device which enables the surgeon to effect a direct control over the motion amplitude and the force of the movable element.

It is another object of the invention to provide higher reliability of the drive which would not require readjustment in the course of surgery.

It is still another object of the invention to reduce the amount of the attending personnel.

It is yet still another object of the invention to decrease the overall dimensions of the device so as to render it portable.

It is likewise an object of the invention to provide a possibility of adjusting the motion amplitude and/or force of the movable element immediately in the course of the working cycle of surgery performed.

It is one more object of the invention to provide quick replacement of the surgical instrument.

It is a further object of the invention to provide a possibility of an adjustable gripping of the tissue operated upon by means of the surgical instrument having a cutting edge, as well as pulling the tissue portion to be resected to a required position.

It is an additional object of the invention to provide conditions for extraction of brittle foreign bodies from the eye.

Such an embodiment of the drive of the proposed ophthalmological device enables the surgeon to effect a direct control over the motion amplitude of the movable element and the force applied thereto.

It is expedient that the closed hydraulic system of the proposed ophthalmological device, comprising a drive with one bellows connected to the movable element, should comprise a second bellows accommodated in the pressure-exerting contrivance, while the first bellows connected to the surgical instrument movable element, be accommodated inside the housing.

The end of the movable element extending from the stationary fixed element may rest upon the end of the bellows accommodated inside the housing.

It is advisable that the movable element be spring-loaded with respect to the bellows accommodated inside the housing, by means of a spring fitted onto the movable element.

It is convenient that the second bellows be interposed between two surfaces that form the pressure-exerting contrivance which is in fact a pedal.

The surgical instrument can be made detachable, while the bellows end against which the movable element butts up serves as a parting face, and forceps or scissors can be made use of as the detachable surgical instrument.

When both of the stationary and movable elements are shaped as tubes of which the inner one has a connector for removing various tissues from a patient's eye, said connector being located on the extending end of the movable element, in the ophthalmological device, according to the invention, the spring fitted on the movable element may have a stop the function of which is performed by the connector.

BRIEF DESCRIPTION OF THE DRAWINGS

Further objects and advantages of the present invention will become obvious from a consideration of some specific exemplary embodiments thereof to be read with reference to the accompanying drawings.

DETAILED DESCRIPTION OF THE INVENTION

Figure 1:
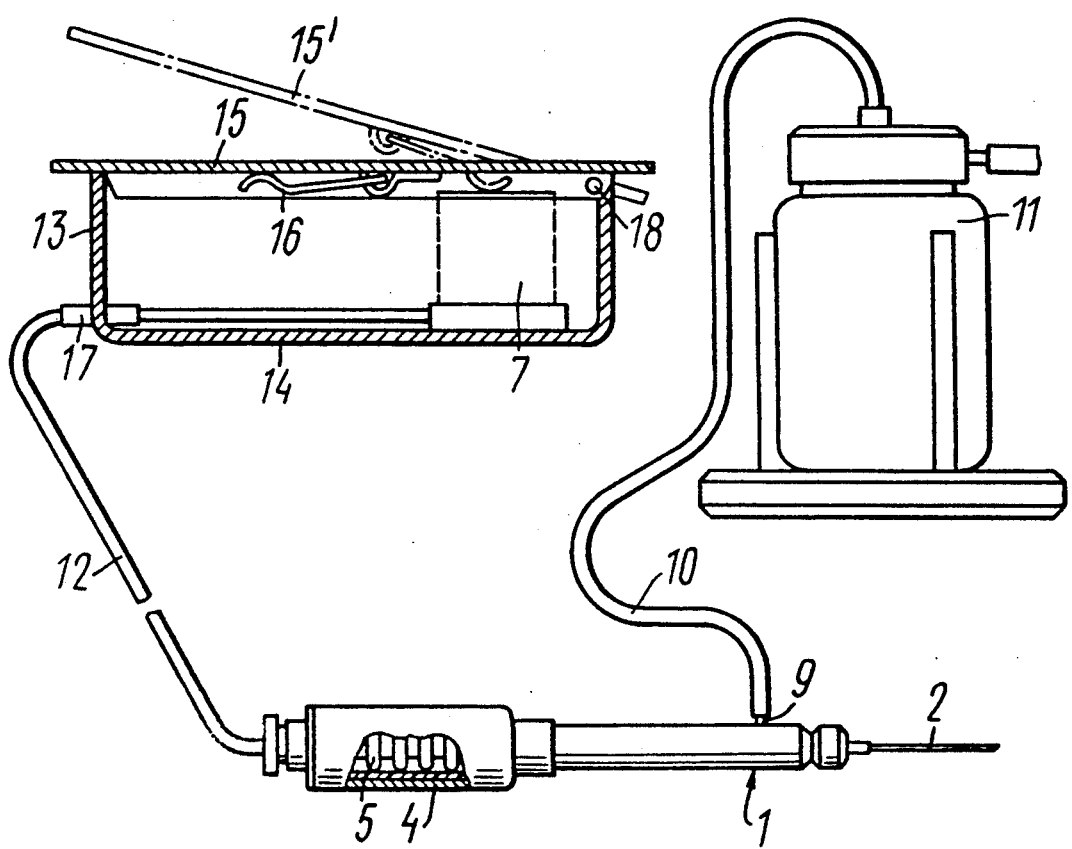
FIG. 1 is a general diagrammatic view of an ophthalmological device, according to the invention.

The ophthalmological device of the present invention comprises a surgical instrument 1 (FIG. 1) and a drive in the form of a closed hydraulic system.

The surgical instrument 1 is made up of two mutually displaceable elements 2 (FIGS. 2, 3) and 3. The element 2 is fixed stationary and connected to a housing 4. The element 3 is movable and connected to the drive which imparts mutual motion to the elements 2 and 3.

The closed hydraulic system comprises a bellows 5 (FIGS. 1, 3) accommodated inside the housing 4 and adjacent to an end 6 of the element 3, and a bellows 7 accommodated in a pressure-exerting contrivance. The element 3 is loaded by a spring 8 (FIG. 3) with respect to the bellows 5, said spring being fitted on the element 3 inside the body 4.

The elements 2 and 3 (FIGS. 2, 3) are shaped as tubes, and the element 3 has a connector 9 for removing resected tissues from the patient's eye. The connector 9 is located on a portion of the element 3 which extends from the element 2 and is adapted to serve as a stop for the spring 8.

The connector 9 (FIG. 1) communicates with an aspirator arrangement 11 through a flexible piping 10.

The closed hydraulic system is established by the bellows 5, the bellows 7, and a flexible piping 12 intercommunicating both bellows; the hydraulic system is filled with a liquid medium, e.g., a mineral oil.

The pressure-exerting contrivance is essentially a pedal 13 defined by surfaces 14 and 15, the bellows 7 being interposed therebetween. A cramp 16 is held to the surface 15 to set the surface 15 in either of the positions, viz., a working position 15' and the transfer position 15.

An elastic sleeve 17 is provided on the piping 12 to prevent it from falling out of the pedal 13 and being jammed by the working surfaces 14, 15 of the pedal 13. The surface 15 has a pivot pin 18 to rotate thereabout.

The movable element 3 (FIG. 2) has a travel restrictor which is in fact a shoulder 19 in the element 3 itself and a shoulder 20 in the stationary element 2, both shoulders interacting when the elements 2 and 3 move relative to each other.

The element 2 has a lug 21 adapted to engage a slot 22 (FIG. 4) to prevent the element 2 from rotation.

Figure 2:
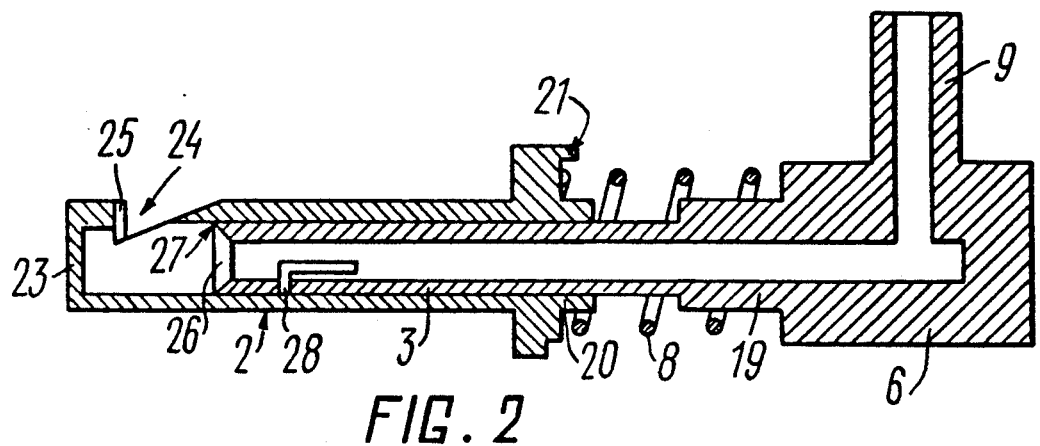
FIG. 2 is a longitudinal sectional view of a surgical instrument which is in fact a vitreotome.

FIG. 2 illustrates the surgical instrument in the form of a vitreotome which has a closed end 23 of the element 2 and a side opening 24 with a cutting edge 27, while the element 3 has an open end 26 with a cutting edge 27. A recess 28 is made in the side wall of the element 3 close to the end 26 to exert a hold-down force on the cutting edges 25 and 27.

A second end 29 (FIG. 3) of the bellows 5 rests upon a nut 30 which is traversable to set a required motion amplitude of the element 3.

The slot 22 (FIG. 4) is helically shaped and is adapted for the connector 9 to move therealong.

Figure 3:
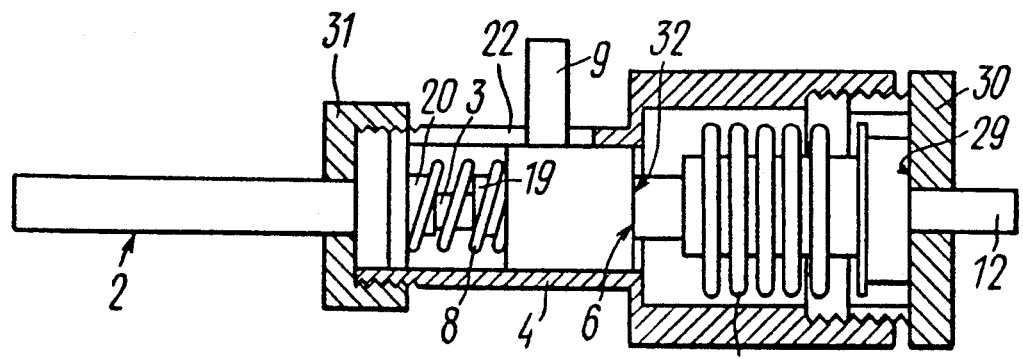
FIG. 3 is a longitudinal sectional view of a handgrip of the device, according to the invention.
Figure 4:
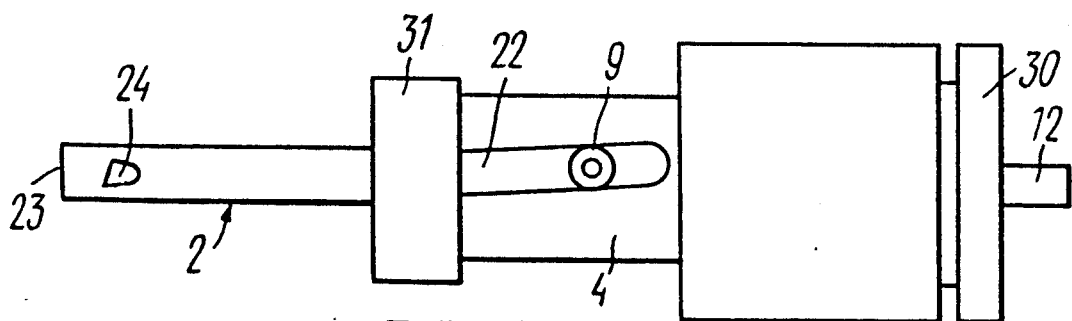
FIG. 4 is a general view of the handgrip of FIG. 3.

The element 2 is locked on the housing 4 by means of a nut 31 (FIGS. 3, 4).

The surgical instrument 1 is made detachable, an end 32 (FIG. 3) of the bellows 5 serving a parting face.

Figure 5:
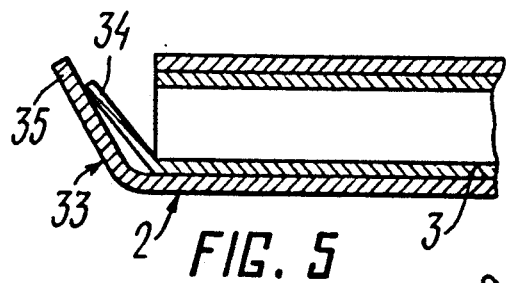
FIG. 5 is a longitudinal sectional view of a surgical instrument made as forceps, according to the invention.

FIG. 5 presents an alternative embodiment of the surgical instrument, viz., in the form of forceps 33, which has jaws 34 and 35 connected to the movable element 3 and the stationary element 2, respectively.

Figure 6:
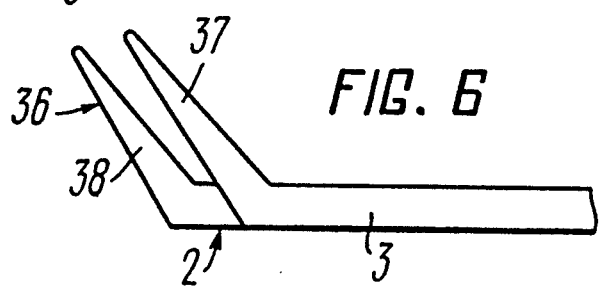
FIG. 6 is a longitudinal sectional view of a surgical instrument made as scissors.

The surgical instrument in the form of scissors 36 (FIG. 6) having blades 37, 38 is of a similar construction.

The ophthalmological device operates as follows.

The instrument 1 is inserted into the patient's eyeball. The surgeon holds the instrument 1 by its housing 4 and brings the free end of the instrument 1 to that portion of the intraocular tissue which is to be resected. Then a negative pressure is admitted to pass through the connector 9 into the interior of the elements 2 and 3 to establish a vacuum therein, with the result that the intraocular tissues located nearby the side opening 24 of the element 2 are sucked into the interior space of the element 2 by virtue of the abovesaid vacuum.

Then the surgeon presses against the surface 15 of the pedal 13, using his foot, thus compressing the bellows 7. Since the liquid filling the hydraulic system is practically incompressible, the bellows 5 is made to elongate accordingly, thus pushing forward the movable element 3 of the instrument 1. While moving the element 3 interacts by its end 26 having the cutting edge 27, with the cutting edge 25 of the side opening 24, thus cutting off the portion of the intraocular tissues that has been sucked into the interior of the element 2, whereupon the thus-resected tissue portion is removed through the connector 9 and the piping 10 into the aspirator arrangement 11. Next the surgeon ceases depressing the pedal 13, and the element 3 and the entire hydraulic system are made to return into the initial position under the action of the spring 8 and by virtue of elastic forces of the bellows 5 and 7.

Thereupon at surgeon's discretion the working cycle may be repeated as many times as required at any frequency and force applied. Whenever necessary the surgeon may hold the entire hydraulic system and hence the element 3 in an extended position, thus closing the side opening 24 in the element 2.

With the instrument 1 made as the scissors 36 or the forceps 33 its operation proceeds practically in a similar way, with the sole exception that the movable jaw 34 or the movable blade 37 moves along with the element 3.

The present device has been tested experimentally on ten isolated cadaveric eyes and the eyes of four test rabbits. After successful trialling the device has been applied clinically during 32 surgical procedures in patients with various intraocular pathologies. A total of 12 surgical procedures have been performed transciliary vitrectomy for unresolvable vitreal hemorrhages and opacity of the vitreous humor, 13 procedures of posterior lensectomy for soft and membranous cataracts of various etiology, and 7 surgeries of phakovitrectomy for penetrating wounds and complicated cataract extractions followed by the formation of a vitreocortical mixture. Four of the surgeries mentioned above have been performed outside the principal clinical base in the course of emergency calls to other medical institutions. There have been employed all the three embodiments of the instrument 1, i.e., guillotine-type vitreotome, scissors, and tubular forceps. In all cases the desired anatomical effect has been attained.

Application of the proposed ophthalmological device offers the following advantages.

The surgeon can easily change the general operational disposal and tactics in the course of surgery, depending on a given situation or, conversely make no changes in the adopted disposal despite unforeseen circumstances, that is, when coarse fibrous adhesions and membranes are encountered the surgeon can increase considerably the force applied to the movable element 3 of the instrument 1; when a danger of intraoperative hypotony threatens, the surgeon can change arbitrarily the opening and closing time ratio of the side opening in the stationary element 2 within the working cycle; or to slow down the motion of the element 3 when manipulating close to the retina, thus reducing the tractive effect on the retina.

The surgeon is enabled to grip the tissue operated upon by a preadjusted force with the use of the surgical instrument 1 having the cutting edge 25 (27), to pull the gripped tissue portion to a required position (e.g., to retract a fibrous membrane from the retina) for its safe resection by further pressing against the pedal 13. In addition, the surgeon is in a position of catching with the forceps 33 any foreign bodies exerting different forces thereon, which is important for catching brittle foreign bodies. The surgeon may keep the side opening in the element 2 closed, which is important for maintaining a balance between the fluid outflow from the eye and its inflow thereinto through an additional instrument. Whenever necessary the surgeon may replace the instrument 1 rapidly, i.e., the vitreotome for the scissors 36 or the tubular forceps, or vice versa. High operational response of the hydraulic drive of the instrument 1 enables the surgeon to respond to any change in the intraocular situation at a high rate. All features mentioned above add considerably to the efficacy of a surgical intervention, since enable the surgeon to attain practically in all cases the anatomical tasks set before surgery.

There is eliminated any risk of undue or inaccurate execution of a surgeon's command by an attendant which is authorized to change, if necessary, the operational mode of the instrument 1 on the control panel (omitted in the Drawing).

There is minimized the risk of failure of the instrument 1 in the course of surgery, since the device is devoid of a complicated electric circuitry and a pneumatic valving system. Besides, the device is independent of power mains in which unforeseen failures are also possible. All these factors add to the safety of a surgical procedure.

The construction of the device is also free from such bulky units as power plant and control panel, which makes it possible to reduce the overall dimensions of the instrument to such an extent that it becomes practically a pocket-type. Compact construction arrangement of the instrument extends considerably the scope of its practical uses and renders it very valuable for urgent surgery in emergency cases.

What is claimed is:

1. An ophthalmological device, comprising:
    a surgical instrument comprising inner and outer, coaxial elements each having surgical means on one end for introduction into and performing a surgical procedure on a patient's eye and an opposite end;
    a housing fixedly connected to the opposite end of the outer element for holding the surgical instrument;
    hydraulic drive means operative in response to hydraulic pressure for moving the inner element relative to the outer element and
    pressure-exerting means for providing the hydraulic pressure, the pressure-exerting means forming a closed hydraulic system with the hydraulic drive means,
    wherein said hydraulic drive means comprises a first bellows accommodated inside said housing and connected to said inner element; a second bellows located in said pressure-exerting means; and piping communicating said first bellows with said second bellows to establish a closed hydraulic system.

2. An ophthalmological device as claimed in claim 1, wherein said first bellows has a free end which is adapted to move upon actuation by liquid in said closed hydraulic system and on which rests the opposite end of said inner element.

3. An ophthalmological device as claimed in claim 1, comprising a spring fitted over said inner element and adapted to load said inner element with respect to said first bellows.

4. An ophthalmological device as claimed in claim 1, wherein said pressure-exerting means is made as a pedal defined by a first surface and a second surface, said surfaces being in an angular position to each other, while said second bellows is interposed between said first surface and said second surface.

5. An ophthalmological device as claimed in claim 1, wherein said surgical instrument is detachable along a face associating it with said end of said first bellows.

6. An ophthalmological device as claimed in claim 3, wherein said surgical instrument is detachable along a face associating it with said end of said first bellows.

7. An ophthalmological device as claimed in claim 3, wherein said pressure-exerting means is made as a pedal defined by a first surface and a second surface, said surfaces being in an angular position to each other, while said second bellows is interposed between said first surface and said second surface.

8. An ophthalmological device as claimed in claim 3, wherein said outer element is a first tube and said inner element is a second tube accommodated inside said first tube coaxially and having connector means extending therefrom for removing tissues from a patient's eye through said second tube, said connector means being located on said inner element for also serving as a stop for said spring.

9. An ophthalmological device as claimed in claim 5, wherein said one ends of said elements are one of forceps and scissors of said surgical instrument.

10. An ophthalmological device as claimed in claim 6, wherein said outer element is a first tube and said inner element is a second tube accommodated inside first tube coaxially and having connector means extending therefrom for removing tissues from a patient's eye through said second tube, said connector means being located on said inner element for also serving as a stop for said spring.

11. An ophthalmological device as claimed in claim 6, wherein said pressure-exerting means is made as a pedal defined by a first surface and a second surface, said surfaces being in an angular position to each other, while said second bellows is interposed between said first surface and said second surface.

12. An ophthalmological device as claimed in claim 6, wherein said one ends of said elements are one of forceps and scissors of said surgical instrument.

13. An ophthalmological device as claimed in claim 8, wherein said pressure-exerting means is made as a pedal defined by a first surface and a second surface, said surfaces being in an angular position to each other, while said second bellows is interposed between said first surface and said second surface.

* * * * *